(12) United States Patent
Moreno González et al.

(10) Patent No.: US 9,125,964 B2
(45) Date of Patent: Sep. 8, 2015

(54) **PHARMACEUTICAL COMPOSITION AND DEVICE FOR PREVENTING, TREATING AND CURING ULCERS ON A DIABETIC FOOT AND OTHER WOUNDS, WHICH INCLUDES SNAIL SLIME FROM THE SPECIES *CRYPTOPHALUS ASPERSUS* OR *HELIX ASPERSA MULLER* AND PHARMACEUTICALLY ACCEPTABLE CARRIERS AND/OR ADDITIVES**

(75) Inventors: Elmo Ernesto Moreno González, Santiago (CL); Nieves Galdames Flores, Santiago (CL)

(73) Assignee: Muciderm S.A., Santiago (CL)

( * ) Notice: Subject to any disclaimer, the term of this patent is extended or adjusted under 35 U.S.C. 154(b) by 114 days.

(21) Appl. No.: 13/980,735

(22) PCT Filed: May 20, 2011

(86) PCT No.: PCT/CL2011/000031
§ 371 (c)(1),
(2), (4) Date: Jul. 19, 2013

(87) PCT Pub. No.: WO2012/097466
PCT Pub. Date: Jul. 26, 2012

(65) Prior Publication Data
US 2013/0309296 A1 Nov. 21, 2013

(30) Foreign Application Priority Data
Jan. 21, 2011 (CL) .................................... 143-2011

(51) Int. Cl.
*A61K 35/618* (2015.01)
*A61K 35/644* (2015.01)
*A61K 36/28* (2006.01)
*A61L 15/44* (2006.01)
*A61L 15/40* (2006.01)
*A61L 26/00* (2006.01)
*A61F 13/06* (2006.01)

(52) U.S. Cl.
CPC .............. *A61L 15/44* (2013.01); *A61F 13/064* (2013.01); *A61K 35/618* (2013.01); *A61K 35/644* (2013.01); *A61K 36/28* (2013.01); *A61L 15/40* (2013.01); *A61L 26/0057* (2013.01)

(58) Field of Classification Search
USPC .......................................... 424/547, 539, 725
IPC .............................. A61K 35/618,35/644, 36/28
See application file for complete search history.

(56) References Cited

U.S. PATENT DOCUMENTS

| | | | | |
|---|---|---|---|---|
| 5,538,740 | A * | 7/1996 | Abad | 424/547 |
| 6,982,247 | B1 * | 1/2006 | Reetz et al. | 514/2.4 |
| 2005/0037034 | A1 * | 2/2005 | Rhoades | 424/401 |
| 2005/0136079 | A1 * | 6/2005 | Burangulov et al. | 424/401 |
| 2005/0266064 | A1 * | 12/2005 | McCarthy | 424/450 |
| 2007/0141168 | A1 * | 6/2007 | Alkazemi | 424/539 |
| 2007/0248633 | A1 * | 10/2007 | Baldo | 424/401 |
| 2010/0233111 | A1 * | 9/2010 | Wang et al. | 424/62 |

FOREIGN PATENT DOCUMENTS

WO  WO 2009/002982  * 12/2008

OTHER PUBLICATIONS

Tsoutsos et al. J. Dermatological Treatment. 2009. vol. 20, pp. 219-222.*
Website document entitled "Are snail creams good for your skin". Feb. 2009. 4-pages. Obtained from http://thebeautybrains.com/2009/02/10/are-snail-creams-good-for-your-skin/.*

* cited by examiner

Primary Examiner — Chris R Tate
(74) Attorney, Agent, or Firm — Gottlieb, Rackman & Reisman PC

(57) ABSTRACT

The present invention is related to a pharmaceutical composition comprising snail slime of *Helix aspersa müller* (*Cryptophalus aspersus*) (5% to 50%) and marigold extract, propolis and/or almond oil and pharmacologically accepted additives for the prevention additives and/or pharmaceutically acceptable excipients to form a formulation of intermediate to high viscosity (200 to 1000 Pa-s). This invention also relates to the use of a composition which can be formed as a cream or a gel, is preferably soaked in gauze, and shaped as a bandage or sock for the treatment and cure of diabetic foot ulcers and other severe wounds, particularly those associated with diabetes, gout, Lesch Nyhan syndrome or other conditions to the skin, including, keratosis, onychomycosis, ringworm, among others.

14 Claims, 3 Drawing Sheets

PHARMACEUTICAL COMPOSITION AND DEVICE FOR PREVENTING, TREATING AND CURING ULCERS ON A DIABETIC FOOT AND OTHER WOUNDS, WHICH INCLUDES SNAIL SLIME FROM THE SPECIES *CRYPTOPHALUS ASPERSUS* OR *HELIX ASPERSA MULLER* AND PHARMACEUTICALLY ACCEPTABLE CARRIERS AND/OR ADDITIVES

FIELD OF THE INVENTION

This invention relates to the use of a composition and device containing snail slime, marigold extract, propolis and/or almond oil and pharmacologically accepted additives for the prevention, treatment and cure of diabetic foot ulcers and other severe wounds, especially those associated with diabetes.

BRIEF DESCRIPTION OF THE INVENTION

The present invention is related to a pharmaceutical composition comprising snail slime of *Helix aspersa müller* (*Cryptophalus aspersus*) (5% to 50%) and additives and/or pharmaceutically acceptable excipients to form a formulation of intermediate to high viscosity (200 to 1000 Pa-s). This composition, which can be formed as a cream or a gel, is preferably soaked in gauze, and shaped as a bandage or sock to be applied over ulcerous wounds or other skin-like conditions. The composition contains natural extracts such as marigold extract, propolis and vegetable oils. Further claimed is the preparation process of the composition and its use for preparing a medicament or device for preventing or treating illnesses of ulcers or poor prognosis wounds generated by metabolic diseases such as diabetes, gout, Lesch Nyhan syndrome or other conditions to the skin, including, keratosis, onychomycosis, ringworm, among others.

DISCUSSION OF PRIOR ART

Diabetes is a chronic non-communicable disease with high prevalence worldwide (6.1 to 8.1/100,000). It is estimated that 150 million people suffer from some form of diabetes, It is estimated that by 2025 there will be 300 million cases, most occurring in developing countries, preferably affecting individuals in the middle of productive age (45-64 years) (ALAD Guides et al, 2007). Chronic hyperglycemia, characteristic of diabetes, affects the long term, the development of nephropathy, retinopathy, neuropathy and cardiovascular complications, which results in high morbidity and mortality of diabetic patients compared to the general population (Ministry of Health, MINSAL, Chile 2005).

Diabetes mellitus type 1 (DM1) is characterized by destruction of pancreatic $\beta$ cells, which results in absolute insulin deficiency and vital dependence on exogenous insulin. It occurs at any age, but the highest incidence is observed in youngsters under the age of 15 years, most commonly in preschoolers, especially pre-pubertal. Its etiology is 90% autoimmune, which is determined by the presence of anti-islet (ICA), anti-GAD and anti-insulin antibodies. About 10% of cases are idiopathic (Ministry of Health, Chile 2005). The prevalence estimated by the World Health Organization (WHO) for 2000 was 6.5%. (King H, et al, 1998.). Taking into account the number of people with DM1 under control in the National Health Services of the Ministry of Health in Chile (MINSAL) of approximately 3,000 (children and adults), the DM type 1 estimated prevalence of 0.5 % of the diabetic population, is significantly lower than global estimates (4 and 6%)(Ministry of Health, MINSAL, Chile 2005).

According to the results of the Multinational Project of Diabetes in Children (DiaMOND), Santiago of Chile have one of the lowest incidence of type 1 DM in the world, 1.6 per 100,000 in children under 14 years old, between 1990-1992. (Karvonen M, et al, 2000).

Based on the National Register of incidence of DM1 in children under 15 years old, conducted by the MINSAL between 1995 and 2000, there was an average of 150 cases per year. To determine the incidence in the entire population, one should add in the incident cases of patients over age 15 (estimated at 30 additional cases), which would give a total of 180 cases per year in the country. It is estimated that approximately 75% of these would be beneficiaries of System of National Services of Health (SNSS), bringing 135 new cases of DM1 each year (Ministry of Health, Chile 2005.)

Diabetes mellitus Type 2 is characterized by insulin resistance, which is usually accompanied by a relative deficiency of insulin (Ministry of Health, Chile 2005).

Diabetes Mellitus Type 2 (DM 2) is frequently asymptomatic, so the diagnosis is made in about 50% of cases for laboratory tests ordered for another reason and not by clinical suspicion. The scant classic symptoms determine, with high frequency, a late diagnosis and the presence of chronic complications. This type of diabetes increases with age, obesity and physical inactivity and usually is associated with other high-risk cardiovascular diseases such as hypertension and dyslipidemia, so inquest to DM is indicated in these individuals (Ministry of Health, MINSAL, Chile 2005).

By 2000, it was estimated that over 35 million people would suffer from DM in the South American continent, with 54% in Latin America and the Caribbean (LAC), with a projected 64 million people in 2025, rising to 62% in the Latin American region (Barceló A & Rajpathak S et al., 2001).

The global demonstrated prevalence by the National Health Survey was 4.2% (4.8% in men and 3.8% in women), which is higher in people older than years old and in poorer women (http://epi.minsal.cl/epi/html/invet/ENS/Informe Final ENS.pdf). To curb the rise in mortality from diabetes was one of the goals that Chile address as part of the Health Objectives for the decade 2000-2010, and the main goal was to keep the age-standardized rate in 14 per 100,000 inhabitants (Ministry of Health, MINSAL, Chile 2002).

Diabetes has a number of complications that can be initiated individually or combined, especially the acute complications (hyperglycemia and hypoglycemia), ophthalmologic, renal, neurologic, diabetic foot, hypertension and dyslipidemia (ALAD Guides et al, 2007).

The Diabetic Foot, as sequel of two most common chronic complications of this disease, peripheral neuropathy and vascular insufficiency, is a condition with high morbidity and therefore it impacts negatively on the quality of life of patients as a result of the frequent admissions, longer hospital stays and amputations. It is estimated that one in ten people in the time of diagnosis of diabetes type 2 (*mellitus*) have risk factors for foot lesions (Boulton, 2005).

The magnitude of the problem is evident considering that over 25% of hospital admissions of diabetics in the U.S., U.K., Spain and Mexico are related to foot problems (Irkovska, 2001; Got, 2001). About 15% to 25% of all diabetic patients will develop a foot or leg ulcer during the course of their disease (Boulton 2005, Pinzur M et al., 2005). Among the associated risk factors are described, patients with long-term Diabetes mellitus (>10 years), age (>50 years), history of ulcer or amputation, presence of neuropathy, arthropathy or vascular disease, presence of other diabetes complications, low socioeconomic status of the patient and social isolation, poor diet, poor education on foot care and other risk factors associated with vascular disease (Gallardo et al 2004, Ministry of Health, Chile 2005). There are few studies on the prognosis and outcome of diabetic foot; however, Chilean surgeons have the perception that the prevalence is increasing (Iribarren O. et al, 2007; Olmos P. et al, 1994).

Diabetic foot is called to that foot of patients that due to alterations characteristic of diabetes, present risk of injuries and/or amputations. These lesions occur especially in high-risk patient, smokers and those with previous vascular complications of lower extremities (Ministry of Health, Chile 2005). As an example, only in the south area of Santiago there are 4,000 diabetic foot patients receiving attention in the 6 medical centers of the Municipal Health Corporation of San Bernardo (Source: Municipal Health Corporation of San Bernardo, Santiago, Chile).

Early detection of diabetic foot is performed through a foot exam, including the use of monofilament, palpation, visual and sensitivity examination. If preventive measures fail and injury occurs or a high-risk foot is confirmed, a multidisciplinary management should be performed, especially in those cases with a history of ulcer or amputation of the other extremity.

For injuries management in the neuropathic diabetic foot, it is used the Wagner classification, where the lesions of 0, I and II grades should be handled at the primary level mainly with resting, non-traditional cures according to standards and oral antibiotic therapy, if required. If no response is observed to these measures, patient should be referred to secondary and tertiary levels, as well as those who have lesions of III, IV or V grades for eventual surgical solution and intravenous antibiotic therapy (Brodsky J W. 2001).

If there is indication of utility of antibiotic therapy, it will typically be an oral monotherapy (1st generation cephalosporins, clindamycin, lincomycin, ampicillin-sulbactam, amoxicillin-clavulanate, ciprofloxacin and other quinolones) for 10-14 days for a mild acquired infection, expanding the spectrum (clindamycin and third generation cephalosporins or quinolones, ampicillin-sulbactam and metronidazole, vancomycin) with a treatment duration of 14-21 days for severe infections (B. Beltran et al., 2001).

In the case of ischemic diabetic foot, all patients should have an initial assessment at the primary level of the health system hierarchy for early detection of risk and another assessment quarterly to prevent episodes. At this level the assessment should include and emphasize education and preventive management and early detection of pediatric cases requiring referral to emergency services. Symptomatic patients are derived to the upper level of health care and those with absence of pulses in one extremity, determining at the tertiary level the procedure to follow (revascularization, amputation or conservative management) (Ministry of Health, MINSAL, 2005.)

Diabetic foot problems are known in medicine, there are many research publications, programs established and investigations described, some of them mentioned in the item "Discussion of prior art" of this application, indicating that diabetic patients without strict treatment will suffer characteristic wounds of diabetic foot, that in a high percentage of cases will result in amputation, thereby leading to large social and economic costs for the patient, his family and the state.

*Helix aspersa Müller*

The common garden snail, *Helix aspersa Müller*, also known as *Cryptophalus aspersusa*, is a gastropod mollusk of the *Pulmonata* order, of terrestrial life. It is one of various species of *Helix*, very similar among them, also called snails. It requires secretion of mucus or slime for its movement, which upon solidification serves as a support that isolates it from an otherwise unfavorable environment. Other names used are *Cryptomphalus aspersus, Cornu aspersum* and *Cantareus aspersus*, I s hermaphrodite, oviparous and has a spiral wound calcareous shell. The slime snail suitable for cosmetic application is obtained from fasting caused by innocuous stimulation (radiation or mechanical stress). This stimulation does not alter the survival of the animal and can be repeated several times during its life cycle. The slime secreted because of this external stimulus has the ability to repair the snail skin and protect it from external aggressions. These properties can be extrapolated to the formulation and implementation of preparations for cosmetic use (Abbot R, 1996).

Snail slime, particularly of the species *Cryptophalus aspersus* or *Helix aspersa Müller*, is mainly composed of the following active principles, considered the most relevant:

Allantoin (glioxil diurea): stimulating agent of the skin cell proliferation. It helps to remove necrotic tissue, replacing them with new tissues. It is an anti-irritant, and promotes and accelerates the natural healing processes in the body. Therefore, it is a stimulant of epithelialization and helps to cleaning and removing necrotic tissue, accelerating the growth of healthy new tissue (Sznitowska Janicki M & S, 1988). The FDA has not recognized allantoin as a wound healing agent, but has recognized it as a skin protector, and has classified it into category I, which means it is safe and effective (www.fda.com).

Glycolic acid (hydroxy acetic acid): It is a natural organic compound of small molecular chain, which allows it to quickly penetrate the skin up to deeper layers. This acid is primarily widely used in skin treatments to fade, in any section of the skin, wrinkles, stretch marks, scars and to reduce acne. As an irritant, it is recommended for use with plant extracts, collagen and vitamins to support cellular reconstruction (Denda S, 2010). The action of this treatment is to decrease the thickness of the stratum corneum of the skin and increase the thickness of stratum malpigio. It is also an excellent exfoliating and helps other components to penetrate the skin easier (M L Elson, 1993 Tribó et al, 2004).

Elastin: It is a 70 KDa protein, present in all vertebrates, with structural features that provide strength and elasticity to the tissues, greatly expanded capacity, allowing the healing by regenerating tissue expansion in the treatment of wounds (Sage & Gray, 1977; Young G L, Jewell D, 2000).

Collagen: This molecule allows replacement of denatured or oxidized collagen and production of metalloproteinase inhibitors (TIMP) which facilitates regulation between synthesis and degradation of the components of the dermis. It also improves cell cytoskeleton structure, since it induces proliferation and activation of fibroblasts by beta-EGF activity. Accordingly, it increases hyaluronic acid, collagen fibers production and elastin deposition in the extracellular matrix fibronectin, so it promotes dermal support (Young G L, Jewell D, 2000).

Finally, natural antibiotics content in the slime snail are substances capable of acting against bacteria usually present on the skin, especially *Escherichia coli, Staphylococcus aureus, Pseudomonas aeruginosa* and *Acne vulgaris*, protecting from its infection. Besides these most relevant components, the presence of vitamins and antibiotics are estimated allowing faster skin regeneration, reduced inflammation and inhibition of infectious processes characteristic of diabetic foot.

In this regard it is particularly noteworthy that the empirical evidence suggests that all components of the snail slime together, particularly the Chilean species (*Helix aspersa müller*), act synergistically, an important aspect to be analyzed within the proposed application.

DETAILED DESCRIPTION OF THE INVENTION

Figure 1:
FIG. 1 is a photograph of the strain snail *Helix aspersa müller*
Figure 2:
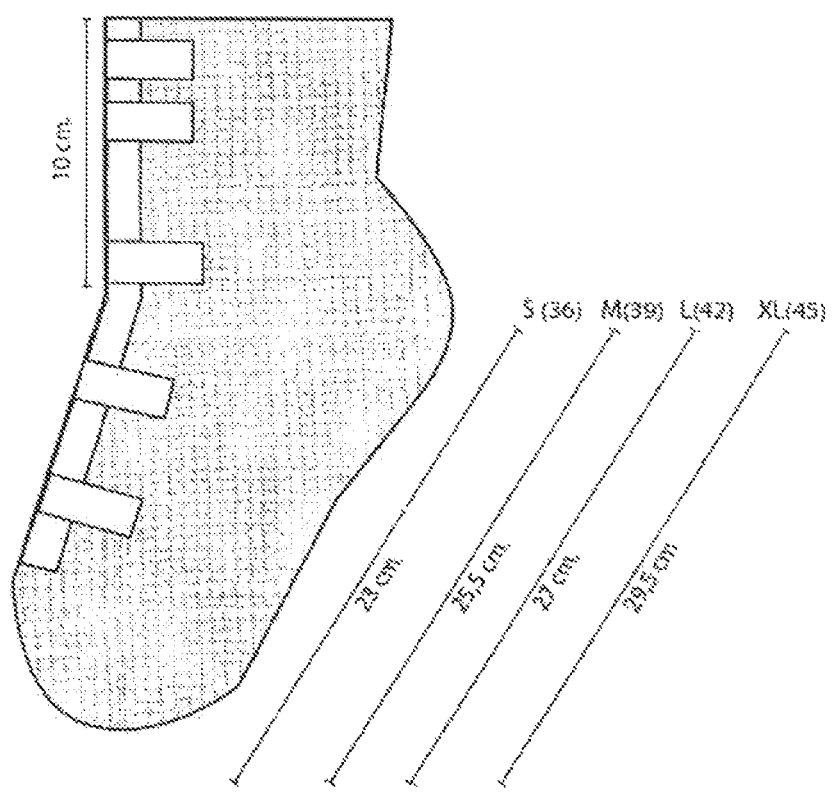
FIG. 2 depicts the shape and size of agauze sock soaked in gel formulation of the invention for therapeutic purposes.
Figure 3:
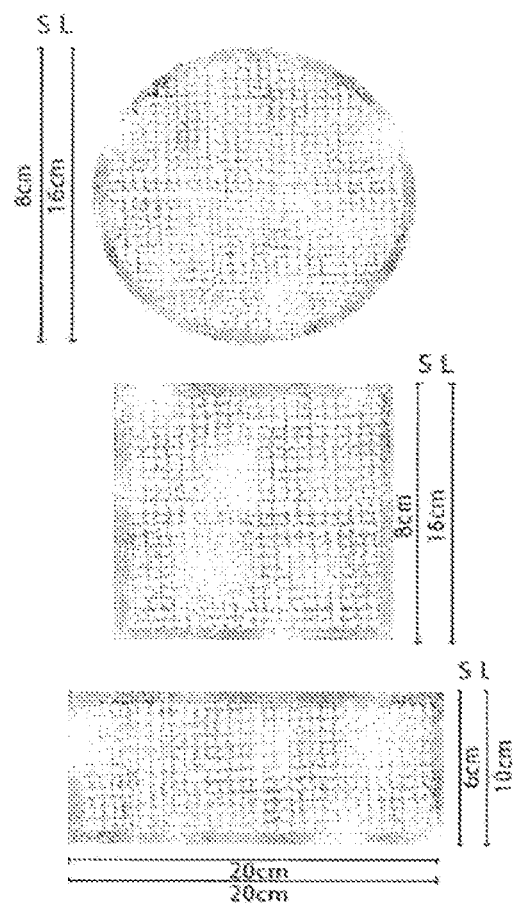
FIG. 3: Shape and dimensions of the various embedded gauze Gel pads of the invention for therapeutic purposes.

From a few years, the applicants of the present invention have been dedicated to the development of products based on snail slime national species. Its development has been eminently cosmetic, generating various products including face cream, hand and body, shampoo, conditioner, bath soaps, all currently registered and marketed.

Considering that the components of the snail slime have healing properties, regenerative and antiseptic, among others, the applicants began to develop a product specifically formulated for healing and regeneration of ulcerated wounds, and particularly, for one of the most complicated cases of this type of wounds, the diabetic foot.

In this regard, it should be noted that 15% of diabetic patients develop a foot ulcer during their lifetime (Pinzur M et al., 2005). As we mention above, diabetic foot is called the foot of those patients that due to alterations characteristic of diabetes, present risk for injuries and/or amputations. These lesions occur especially in high-risk patient, smokers and those with previous vascular complications of lower extremities (Ministry of Health, Chile 2005).

The main problem of this disease for any country is the high cost. The effects of the topical product that involves this project aims eventually to provide an effective and easily administrable treatment to diabetic foot wounds, which allows in the short and medium term:

Reducing the number of amputations and disability days,
Reduction of medical hours used in the follow-up,
Reduction of overhead costs (personal and public service) by attention to diabetic foot patients in the country, and
Improving of quality of life for patients and their families.

In summary, the problem being addressed is a major cause of morbidity and is also a chronic complication of Diabetes mellitus that affects the quality of life of patients, which generates disabling as a result of surgical treatment that sometimes is necessary so as not to compromise the patient's life.

Therefore, the formulation disclosed in this application, is aimed at a problem (disease) of patients who are initially diagnosed with Diabetes. These patients may suffer from disorders that can be classified as non-ulcerating or ulcerating wounds in the lower extremities (feet). This is the main source of the problem, and the product we develop becomes our opportunity to be a complementary alternative to the treatments currently applied to diabetic foot patients in Chile, hoping to generate savings to 3.75% of the country spending per year in this disease which it is estimated is about US$200 million. Therefore, we believe, the health centers will decrease their costs by using the product.

The inventors of the present application initially assessed the product as dermo-cosmetic, as part of popular use being given to the snail slime, clearly taking advantage of its extraordinary qualities that have been displayed on a large number of people with different conditions to skin, especially in patients with some type of disorder in the lower extremities (feet). The product has been used as a complement to healing diabetic foot treatments in over 100 patients with this condition. Surprisingly it has been observed that the formulation in study performs functions not only palliative but curative of diabetic foot, especially in more complex cases for its advanced state of ulceration. Therefore, it is clear that the slime snail has an activity that stands out to conventional treatment.

The prophylactic and therapeutic continuous use of this specific formulation of snail slime (*Helix aspersa* Müller species) significantly decreases the incidence and prevalence rate of wounds, allows prevention, treatment and wound healing in an advanced stage, particularly those related with ulcers of diabetic foot. This can increase the chances of healing of patients, decrease the percentage of amputations and ultimately improve the quality of life of people in that condition.

The present invention is further directed to the development of an application/device of a finished product, which will be more efficient and effective than current treatment, which is essentially palliative and generic, with conventional nursing cares. This treatment may, in the best case, arrest the development of the wound. The use of our product may allow further peeling of dead skin and regeneration new skin due to the properties of its components.

The product can be run or installed by the same patient, ie, the patient does not need to move and requires no other human resources associated with the treatment of diseases that are used in a medical center (nurse, administrative staff, physician on duty). This is where the product generates savings. For maximum effectiveness, our device incorporates a monograph of use with appropriate indications.

The product/composition may be used as an application to a sock or as a device including a diabetic sock (FIG. 1), is easy to use by both qualified personnel and the patient, and can be applied to variously sized individuals. Its use is complementary to any other treatment.

Discussion of prior art has concluded that there is not a national or worldwide similar alternative to this product, so this would be novel, inventive and with a certain industrial application, the three fundamental aspects for acceptance of a patent application. Both the design and the application forms are not obvious because in previous analyses we have observed greater effectiveness of the sock versus the cream or gel applied to the ulcerative skin, which exposed to the environment undergoes chemical, photochemical or microbiological transformation, decreasing the effectiveness and time of therapeutic utility.

The ultimate beneficiaries of the solution presented by this application will be the primary care centers, dependent on the municipalities, private clinics, hospitals and all patients mainly with diabetic foot. This invention will also benefit patients who exhibit other disorders such as wound infections, onychomycosis (usually painless fungal infection, characterized by affecting potentially all toenails and produce deformities and color change), ringworm (fungus on skin where there is itching, redness, blisters, cracks and sores in some cases changes color with exposure to heat and humidity), hyperkeratosis (thickening of the stratum corneum, with varying degrees of acanthosis, leading to what is popularly known as "callus"), ulcers by friction or pressure.

It is important to highlight that the suitable formulation also comprises marigold extract, propolis and/or almond oil, excipients and/or pharmaceutically acceptable additives, which are the basis of a synergistic effect observed which gives higher efficacy of the formulation due to its cosmetic properties.

The contribution of the product is relevant to public health, since this product is able to stop and reverse the regular process of advancing a patient's wounds (ulcers) of diabetic foot, it will improve quality of life, reduce treatment costs and use of biomedical staff time in treatment, avoid amputations in a significant percentage, preventing the increase of disabled people in our country and avoiding disruption of family and social environment. It is estimated that the use of the product could allow at least 3.75% savings in annual spending in this disease, which as stated above is estimated at approximately $200 million annually just in Chile (Source: Funds capital angels, Faculty of Economics and Business, University of Chile).

EXAMPLES

The following examples are preferred but not exclusive of our invention:

Example 1

Example of Formulation a) Formulation of the Basal Cream

| INGREDIENT NAME | PERCENTAGE (%) |
|---|---|
| water | 73.50 |
| Filtered snail slime | 5.00 |
| Liquid Paraffin | 6.00 |
| Glycerib ® | 5.00 |
| Cetearth-20 ® | 3.00 |
| Hydrogenated Polyisobutene | 3.00 |
| Dimethicone | 1.00 |
| Glyceril/PEG-100 stearate | 1.00 |
| Propylene glycol | 0.56 |
| Tocopherol Acetate | 0.50 |
| Diazotidinil urea | 0.30 |
| Methylparaben | 0.26 |
| Crosslinked alkyl acrylate polymer | 0.20 |
| DMDM Hydantoin | 0.14 |
| Propylparaben | 0.03 |
| Iodo propynyl butyl carbamate | 0.01 |
| Triethanolamine | 0.30 |
| Marigold extract | 3.00 |
| Almond oil | 3.00 | b) Gel Formulation
1. 50 g Laboratory cream Bellcos
2. 30 g of sterile snail slime
3. 10 g of vaseline
4. 10 mL of bi-distilled water or normal saline Example 2

Example of Formulation

Manufacture of a Gel for 15 to 20 Gauze Sock-shaped 50 grams of body cream are sterilized by autoclaving at 150° C. with a temperature rise time, exposure time and cooling time (30 minutes each), and then 30 grams of sterilized *Helix aspersa Muller* slime is added, afterwards it is homogenized with stirring, next 10 grams of petrolatum and 10 mL of bi-distilled water are added to maintain humidity. Finally, the cream is homogenized with marigold extract, propolis and/or almond oil and then the gauzes are subjected to soaking into gel formulation.

Example 3

Administration and Dosage

The product is applied as a gauze band or sock directly on the wound in the following manner:
Case 1: Wound Surface: wash the wound with normal saline serum and then placed the plaster (gauze band) containing our formula and every three days should be monitoring the evolution.
Case 2: Deep wounds (ulcers): wound is washed with normal saline serum, applied the gel, in areas of the wound that has no contact with the gauze band and depending on the location of the wound is placed a sock. If the deep wound (ulcer) is located in the heel of the foot, it is recommended to use the sock. Evolution is observed every 3 days.

Example 4

Application Example

We conducted a case study in podiatric clinics and centers in the municipality of San Bernardo, Santiago, Chile, according to the procedure described in Example 3. This study yielded the following results: of 104 documented cases (33 cases with clean wounds, 31 cases with infected wounds, 10 cases with onychomycosis, 10 cases with ringworm, 10 cases with hyperkeratosis and 10 cases with rubbing or pressure ulcers), 100% of patients showed a clear recovery/healing their wounds with the use of a formulation with snail slime, it is statistically better than the results obtained with conventional treatment alone. It was also possible to infer that the application mode significantly influence the effectiveness of treatment, because when a sub-group of patients were given the formulation by the foot bandaged the results were better in over 50% of cases in terms of curation.

REFERENCES

Boulton Andrew. El pie diabético: epidemiología, factores de riesgo y atención. Diabetes Voice, Noviembre 2005 Vol. 50 Núm. especial, US Pharmacopea, XXIII Brodsky J W. An improved method for staging and clasification of foot lesions on diabetic patients en "The diabetic foot", Cap. 11. Bowker J H., Pfeifer M A., 6th ed. Mosby 2001; 273-282.).

Denda S, Denda M, Inoue K, Hibino T. Glycolic acid induces keratinocyte proliferation in a skin equivalent model via TRPV1 activation. J DermatolSci. 2010 February; 57(2):108-13. Epub 2010 Jan. 8.

Iribarren O., Ais. Gabriela Passim., Natalia Aybar M., Drs. Paulo Ríos M., Lain González A., Marco A Rojas G., Fernando Saavedra P. Pie diabético: Evolución en una serie de 121 pacientes Rev. Chilena de Cirugía. Vol 59-N"5, Octubre 2007; págs. 337-341.

Elson M L. The molecular structure of glycolic acid and its importance in dermatology. Cosmetic Dermatology; 6(7): 35-40, 1993.

Got I. Necessary multidisciplinary management of diabetic foot. J Mal Vasc 2001; 26(2):130-4.

Guías ALAD de diagnóstico, control y tratamiento de la diabetes *Mellitus tipo* 2, ALAD Asociación latinoamericana de diabetes, 2007,pág.: 50-52.

Irkovska A. Care of patients with the diabetic foot syndrome based on an international consensus. CasLekCesk 2001; 140(8):230-3.

Karvonen M, Viik-Kajander M, Molichanova E et al, for The Diabetes Mondiale (DiaMOND) Project Group: Incidence of Childhood Type 1 Diabetes Worldwide. Diabetes Care 21:10, 2000. 1516-26).

Ministry of Health, MINSAL, Clinical Guidelines, Advanced Healing of diabetic foot ulcers, Chile, September 2005.

Ministry of Health, MINSAL, Clinical Guidelines Diabetes Mellitus II. 1st Ed. Santiago: Minsal, Chile 2005.

Ministry of Health, MINSAL, Clinical Guidelines Diabetes Mellitus I. 1st Ed. Santiago: Minsal, Chile 2005.

Ministry of Health. MINSAL, Health Objectives for the Decade 2000-2010. Division of steering role and health regulations, department of epidemiology. First Edition, Chile, October 2002.

Olmos P, Catalán S, Roberts C, O'Dorisio T, Aburto M. Buscando indicadores de riesgo de pie diabético. Parte II. RevChilCir 1994; 46: 552-582.

Pérez Y, Menéndez R, Gamez R Mas R, González R M y Mas R Efectos de la administración oral de D-004 (400 mg/kg) sobre la peroxidación lipídica en ratas ovariectomizadas. Rev GENIC Cien Biol. 36(No. Especial), 2005.

Pinzur M, Freeland R, Juknelis D. The association between body mass index and foot disorders in diabetic patients.

Sage E H & Gray W R 1977 Evolution of elastin and elastin structure, p 291. in; Advances in Experimental Medicine and Biology, vol. 79 LB Sandberg & C Franzblaw, eds) Plenum Press, NY & London).

Sznitowska M, JanickiS. The effect of vehicle on allantoin penetration into human skin from an ointment for improving scar elasticity. Pharmazie.1988 March; 43(3):218.

Tribó M J, Parrado C, Rais B et al. Resultados preliminares de la eficacia del tratamiento intensivo con la secreción de Cryptomphalusasperso (SCA) en la terapéutica del foto envejecimiento cutáneo. Med CutanIberLat Am. 2004; 32:265-270.

Young G L, Jewell D. Creams for preventing stretch marks in pregnancy. Cochrane Database Syst Rev. 2000; (2): CD000066.

The invention claimed is:

1. A pharmaceutical composition for treating a diabetic foot wound comprising:
   15% to 30% snail slime from *Helix aspersa Muller* (*Cryptophalus aspersus*) dissolved in a body cream base;
   3-5% marigold extract; and
   3-5% of at least one of propolis and almond oil;
   wherein said composition has a viscosity of 200 to 1000 Pa-s.

2. The pharmaceutical composition according to claim 1, wherein the viscosity is between 500-1000 Pa-s.

3. The pharmaceutical composition of claim 1, wherein the base includes a carrier medium, and wherein said carrier medium is a gel.

4. The pharmaceutical composition of claim 1, wherein the base includes a carrier medium, and wherein said carrier medium is a cream.

5. The pharmaceutical composition of claim 1, wherein the composition is incorporated within a dressing, and wherein the dressing is gauze.

6. The pharmaceutical composition of claim 1, wherein the composition is incorporated within a dressing, and wherein the dressing is a sock.

7. A method of treating a diabetic foot wound comprising the steps of:
   soaking a dressing in a solution, and applying the dressing to the wound,
   wherein said solution comprises:
      15% to 30% snail slime from *Helix aspersa Muller* (*Cryptophalus aspersus*) dissolved in a body cream base;
      3-5% marigold extract; and
      3-5% of at least one of propolis and almond oil,
   wherein said solution has a viscosity of 200 to 1000 Pa-s.

8. The method of claim 7, wherein the base includes a carrier medium which is a cream.

9. The method of claim 7, wherein the base includes a carrier medium which is a gel.

10. The method of claim 7, wherein the dressing is gauze.

11. The method of claim 7, wherein the dressing is a sock.

12. A method of preparing a dressing for treating a diabetic food wound comprising the steps of:
   chilling a sterilized body cream base;
   adding snail slime from sterilized *Helix aspersa Muller* (*Cryptophalus aspersus*) to the chilled body cream base thereby forming a mixture;
   adding marigold extract at 3-5% by weight to the mixture;
   adding at least one of propolis and almond oil at 3-5% by weight to the mixture;
   adding liquid Vaseline and bi-distilled water to the mixture;
   homogenizing the mixture until a cream or gel is formed; and
   permeating a sterilized dressing with said cream or gel.

13. The method of claim 12, where said dressing is a gauze bandage.

14. The method of claim 12, where said dressing is a wearable sock.

* * * * *